US012728172B2

(12) United States Patent
Evans et al.

(10) Patent No.: US 12,728,172 B2
(45) Date of Patent: Sep. 8, 2026

(54) SPERM NUCLEI AND METHODS OF THEIR MANUFACTURE AND USE

(71) Applicant: Inguran, LLC, Navasota, TX (US)

(72) Inventors: Kenneth Michael Evans, College Station, TX (US); Thomas B. Gilligan, College Station, TX (US)

(73) Assignee: Inguran, LLC, Navasota, TX (US)

( * ) Notice: Subject to any disclaimer, the term of this patent is extended or adjusted under 35 U.S.C. 154(b) by 1093 days.

(21) Appl. No.: 17/863,202

(22) Filed: Jul. 12, 2022

(65) Prior Publication Data

US 2022/0339298 A1 Oct. 27, 2022

Related U.S. Application Data

(62) Division of application No. 16/379,408, filed on Apr. 9, 2019, now Pat. No. 11,413,358.

(60) Provisional application No. 62/673,668, filed on May 18, 2018, provisional application No. 62/655,040, filed on Apr. 9, 2018.

(51) Int. Cl.

| | |
|---|---|
| ***C12N 5/076*** | (2010.01) |
| ***A61K 49/00*** | (2006.01) |
| ***G01N 1/30*** | (2006.01) |
| ***G01N 15/10*** | (2024.01) |
| ***G01N 15/14*** | (2024.01) |
| ***G01N 15/149*** | (2024.01) |
| ***G01N 21/64*** | (2006.01) |
| ***G01N 33/50*** | (2006.01) |

(52) U.S. Cl.

CPC .......... *A61K 49/0017* (2013.01); *C12N 5/061* (2013.01); *G01N 15/1012* (2013.01); *G01N 15/14* (2013.01); *G01N 21/6486* (2013.01); *G01N 33/5005* (2013.01); *G01N 1/30* (2013.01); *G01N 2015/1006* (2013.01); *G01N 15/1459* (2013.01); *G01N 15/149* (2024.01)

(58) Field of Classification Search

CPC ....... C12N 5/061; G01N 21/6486; G01N 1/30

See application file for complete search history.

(56) References Cited

U.S. PATENT DOCUMENTS

| | | | |
|---|---|---|---|
| 5,135,759 | A | 8/1992 | Johnson |
| 5,985,216 | A | 11/1999 | Rens |
| 6,071,689 | A | 6/2000 | Seidel et al. |
| 6,149,867 | A | 11/2000 | Seidel et al. |
| 6,263,745 | B1 | 7/2001 | Buchanan et al. |
| 6,357,307 | B2 | 3/2002 | Buchanan et al. |
| 7,335,507 | B2 | 2/2008 | Anzar et al. |
| 7,371,517 | B2 | 5/2008 | Evans et al. |
| 7,799,569 | B2 | 9/2010 | Durak |
| 8,623,658 | B2 | 1/2014 | Graham et al. |
| 9,347,038 | B2 | 5/2016 | Lenz et al. |
| 2014/0099628 | A1 | 4/2014 | Evans et al. |

FOREIGN PATENT DOCUMENTS

| | | | |
|---|---|---|---|
| EP | 0471758 | A1 | 2/1992 |
| WO | 9013303 | A1 | 11/1990 |
| WO | 99/33956 | A1 | 8/1999 |
| WO | 01/37655 | A1 | 5/2001 |
| WO | 01/85913 | A2 | 11/2001 |
| WO | 02/41906 | A2 | 5/2002 |
| WO | 2004/088283 | A2 | 10/2004 |
| WO | 2011/123166 | A2 | 10/2011 |
| WO | 2013049631 | A1 | 4/2013 |
| WO | 2014/055112 | A1 | 4/2014 |
| WO | 2014/055773 | A2 | 4/2014 |
| WO | 2014142924 | A1 | 9/2014 |

OTHER PUBLICATIONS

Quan et al., Effects of Hoechst33342 staining on the viability and flow cytometric sex-sorting of frozen-thawed ram sperm. Cryobiology, 70(1) pp. 23-31 (Year: 2015).*

Lu et al., (Sep. 2006) Identification of X- and Y-chromosome bearing buffalo (*Bubalus bubalis*) sperm. Animal Reproduction Science, 95(1-2) pp. 158-164 (Year: 2006).*

Srivaidayapong et al., (Feb. 2000) Effect of sperm diluents on the acrosome reaction in canine sperm. Theriogenology, 53(3) pp. 789-802 (Year: 2000).*

Buranaamnuay, K., (2013) Sperm-TALP: An alternative extender for retrieving and diluting epididymal sperm in the domestic cat. Repro Dom Anim, 48(6): pp. 912-917 (Year: 2013).*

International Search Report and Written Opinion issued on Jul. 11, 2019 in related International Application No. PCT/US19/26617.

International Search Report and Written Opinion issued on Jul. 26, 2019 in related International Application No. PCT/US19/26615.

Johnson et al. "Sex Preselection: High-Speed Flow Cytometric Sorting Of X And Y Sperm For Maximum Efficiency." Theriogenology. Dec. 1999, vol. 52, No. 8, pp. 1323-1341.

Amaral et al. "Human Sperm Tail Proteome Suggests New Endogenous Metabolic Pathways. Molecular and Cellular Proteomics." Feb. 2013, Epub Nov. 15, 2012, vol. 12, No. 2; pp. 330-342.

Barroso et al. "Sperm Flow Cytometry: Beyond Human Fertilization and Embryo Development." Aug. 24, 2016. Flow Cytometry.

Lewalski, H. et al. "Flow Cytometric Detection of Unbalanced Ram Spermatozoa from Heterozygous 1;20 Translocation Carriers." Cytogenet Cell Genet. 1993;vol. 64(3-4), p. 286-91.

Larsen et al. "High Resolution DNA Flow Cytometry Of Boar Sperm Cells In Identification Of Boars Carrying Cytogenetic Aberrations." Theriogenology, vol. 62, Issues 3-4, Aug. 2004, pp. 501-551.

Canadian Office Action dated Issued in Aug. 30, 2021 in related CA Appl. No. 3,096,537.

Leahy et al. "Sperm Surface Changes and Physiological Consequences Induced by Sperm Handling and Storage." Reproduction, 142, pp. 759-778, 2011.

European Search Report and European Search Opinion issued in Nov. 25, 2021 in related EP Appl. No. 19786115.6.

(Continued)

*Primary Examiner* — Kara D Johnson

(74) *Attorney, Agent, or Firm* — Ryan Christensen; Hashim Rahman

(57) ABSTRACT

The invention encompasses a rapid and safe preparation method of sperm nuclei, improved sperm nuclei and a method of using the improved sperm nuclei to calibrate a flow cytometer with higher accuracy.

5 Claims, 8 Drawing Sheets

(56) References Cited

OTHER PUBLICATIONS

Peker et al. "Effects of Ultrasonication on Damaged Spermatozoa and Mitochondrial Activity Rate", Turkish Journal Of Veterinary And Animal Sciences, vol. 40, Oct. 2, 2015, pp. 195-199.
Yamamoto et al. "Flow Cytometric Detection and Analysis of Tailless Sperm Caused by Sonication or A Chemical Agent.", Journal of Toxicological Sciences., vol. 25, No. 1, Jan. 1, 2000, pp. 41-48.
U.S. Office Action Issued on Sep. 14, 2021 in related U.S. Appl. No. 16/379,408.
U.S. Office Action Issued on Jan. 10, 2022 in related U.S. Appl. No. 16/379,408.
U.S. Notice of Allowance Issued on Apr. 13, 2022 in related U.S. Appl. No. 16/379,408.
Canadian Office Action dated Issued in Aug. 10, 2023 in related CA Appl. No. 3,096,537.
EP Office Action issued on Apr. 26, 2024, in related EP Appl No. 19786115.6, filed on Sep. 24, 2020.

* cited by examiner

SPERM NUCLEI AND METHODS OF THEIR MANUFACTURE AND USE

REFERENCE TO RELATED APPLICATIONS

This application is a Divisional of U.S. patent application Ser. No. 16/379,408 filed Apr. 9, 2019, which claims the benefit of U.S. Provisional Patent Application No. 62/655,040 filed Apr. 9, 2018, and U.S. Provisional Patent Application No. 62/673,668 filed May 18, 2018. The entire disclosures of which are incorporated herein by reference.

BACKGROUND OF THE INVENTION

Sperm nuclei are generally desired for optimal calibration of flow cytometers used for sperm cell analysis or cell sorting. This is because sperm nuclei are devoid of a midpiece and tail, and as a result, more readily achieve optimal orientation when subjected to orienting forces by a flow cytometer, which in turn results in higher quality signal generation. Unfortunately, the manufacture of nuclei has posed several problems, including the need for centralized manufacture (which in turn may create regulatory issues when exported into foreign jurisdictions), the need to pool sperm cell samples from multiple animals (often times a hundred or more animals), the need to use hazardous chemicals such as azide in order to preserve the sperm nuclei for long term storage and holding, and lengthy manufacturing times involving multiple processes and steps. Additionally, once these sperm nuclei are manufactured, they often yield suboptimal signal generation by the flow cytometer on which they are used, which in turn results in suboptimal calibration or a calibration process that can take an hour or more instead of minutes. This also results in a decrease in productivity with respect to sperm cell analysis and sorting processes.

Accordingly, there is a need for improved sperm nuclei as well as improved methods for their manufacture.

SUMMARY OF THE INVENTION

One embodiment of the invention comprises a composition comprising unsorted sperm nuclei and a DNA selective dye, wherein the composition has been sonicated.

In another embodiment, the invention comprises a composition comprising unsorted sperm nuclei, an aggregation-reducing compound and a DNA selective dye, wherein the composition has been sonicated.

Another embodiment of the invention comprises a method of processing sperm cells comprising providing an unsorted sperm cell sample; combining a DNA selective dye with the unsorted sperm cell sample to create a sperm cell mixture; and sonicating the sperm cell mixture to create stained sperm nuclei. In a further embodiment, the step of combining also includes combining an aggregation-reducing compound with the unsorted sperm cell sample to create a sperm cell mixture.

In yet a further embodiment, the invention comprises a method of processing sperm cells comprising providing an unsorted sperm cell sample; combining a DNA selective dye and an aggregation-reducing compound with the unsorted sperm cell sample to create a sperm cell mixture; and sonicating the sperm cell mixture to create optimally stained sperm nuclei.

An additional embodiment of the invention comprises a method of calibrating a flow cytometer comprising providing a sperm cell sample; combining a DNA selective dye with the sperm cell sample to create a sperm cell mixture; sonicating the sperm cell mixture to create stained sperm nuclei; entraining the stained sperm nuclei in a stream in the flow cytometer to generate a signal; and calibrating the flow cytometer based on the signal generated with the stained sperm nuclei. In a further embodiment, the step of calibrating comprises aligning excitation and emission paths in the flow cytometer. In an even further embodiment, aligning comprises adjusting a beam-shaping optic parameter, a nozzle parameter or a forward fluorescence parameter in the flow cytometer. In another embodiment, the method does not include a step of purifying (i.e., removing sperm tails and midpieces from the sonicated mixture). In yet another embodiment, the sperm cell sample is an unsorted sperm cell sample.

Another embodiment of the invention comprises a method of calibrating a flow cytometer comprising providing a sperm cell sample; combining a DNA selective dye and an aggregation-reducing compound with the sperm cell sample to create a sperm cell mixture; sonicating the sperm cell mixture to create optimally stained sperm nuclei; entraining the stained sperm nuclei in a stream in the flow cytometer to generate a signal, or one or more signals; and calibrating the flow cytometer based on the signal, or one or more signals, generated with the stained sperm nuclei. In a further embodiment, the step of calibrating comprises aligning excitation and emission paths in the flow cytometer. In an even further embodiment, aligning comprises adjusting a beam-shaping optic parameter (such as its position), a nozzle parameter (such as its position or the angle of the stream produced by the nozzle) or a forward fluorescence parameter (such as gain or voltage of the forward fluorescence detector, the position of the forward fluorescence detector or the position of the forward fluorescence collection objective) in the flow cytometer. In another embodiment, the method does not include a step of purifying (i.e., removing sperm tails and midpieces from the sonicated mixture). In yet another embodiment, the sperm cell sample is an unsorted sperm cell sample. In a further embodiment, the flow cytometer is processing more than 60,000; 50,000; 30,000, 20,000; 15,000; 10,000; 5,000; 1,000; 500; 300; 200; 100; or 50, events per second when generating the signal.

In a further embodiment of any of the aforementioned embodiments, the sperm sample, or the sperm nuclei, are obtained or derived from one male.

In a further embodiment of any of the aforementioned embodiments, the sperm cell sample, or sperm nuclei, are obtained or derived from a non-human mammal.

In a further embodiment of any of the aforementioned embodiments, the sperm cell sample, or sperm nuclei, are obtained or derived from a bovid or a suid.

In a further embodiment of any of the aforementioned embodiments, the aggregation-reducing compound is selected from the group consisting of: egg yolk, iodixanol, lecithin, bovine serum albumin, gelatin, collagen or hydrolyzed collagen, macromolecules such as arabinogalactan, and chemically defined polyethylene or polypropylene glycols.

In a further embodiment of any of the aforementioned embodiments, the aggregation-reducing compound is egg-yolk.

In a further embodiment of any of the aforementioned embodiments, the temperature of the sperm cell composition during sonication is more than 35° C., 40° C., 45° C., 50° C. or 60° C.

In a further embodiment of any of the aforementioned embodiments, the sperm cell composition also includes a buffer selected from the group consisting of: TRIS citrate, sodium citrate, sodium bicarbonate, HEPES, TRIS, TEST, MOPS, KMT and TALP.

In a further embodiment of any of the aforementioned embodiments, the beam-shaping optic parameter includes the location of the beam shaping optic.

In a further embodiment of any of the aforementioned embodiments, a nozzle parameter includes the location of the nozzle, the angle of the nozzle or the angle of the stream produced by the nozzle.

In a further embodiment of any of the aforementioned embodiments, a forward fluorescence parameter includes the location of the forward fluorescence detector or the location of the forward fluorescence collection objective.

DETAILED DESCRIPTION OF THE INVENTION

Figure 1:
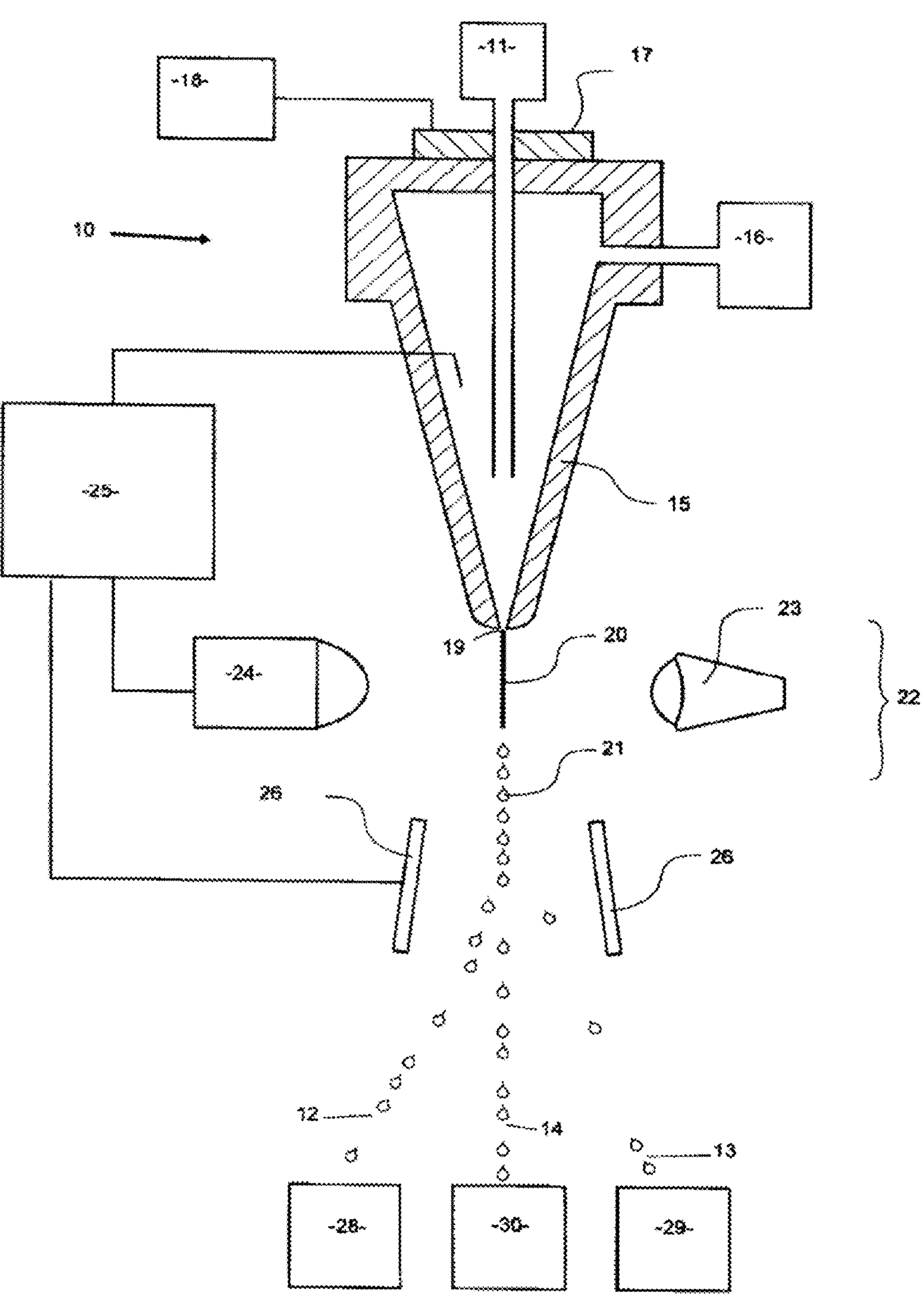
FIG. 1 is a schematic depiction of a jet-in-air flow cytometer.

The invention encompasses a rapid and safe preparation method of sperm nuclei, improved sperm nuclei and a method of using the improved sperm nuclei to calibrate a flow cytometer.

Obtaining a Sperm Cell Sample to Prepare into Sperm Nuclei

It is contemplated that intact viable bovine, porcine, equine, ovine, cervine, murine or other mammalian sperm, may be collected for use with the invention. Various methods of collection of viable sperm are known and include, for example, the gloved-hand method, use of an artificial vagina, and electro-ejaculation. Sperm cell samples for use in the invention can comprise sperm cells from only one male, or in other embodiments, can comprise sperm cells from one or more males. The phrase "unsorted sperm cell sample" means that the sperm cells comprising the sperm cell sample have not been subjected to a cell or particle sorting process. The term "cell or particle sorting process" includes, but is not limited to, physically separating a cell or particle subpopulation from a cell or particle population, or ablating or photo-damaging undesired cells or particles in a cell or particle population whether or not the ablated or photo-damaged cells or particles are removed from the population, via flow cytometer. The term "flow cytometer" as used herein includes but is not limited to flow cytometers, such as jet-in-air flow cytometers, and microfluidic devices, such as microfluidic chips.

One embodiment of the invention encompasses obtaining a raw ejaculate (i.e., neat semen) for use with the invention. Alternatively, prior to use with the invention, the raw ejaculate can be diluted, or extended, in a media. The term "sperm cell sample" encompasses both a raw ejaculate and a diluted, or extended, ejaculate, as well as a sperm-containing semen derivative obtained by centrifugation or the use of other means to separate semen into fractions. As an example, a bovine sperm sample, typically containing about 0.5 to about 10 billion sperm per milliliter, may be collected directly from the source mammal, or from more than one source mammal of the same species, into a vessel containing an extender to form an extended sperm cell sample. An extender may optionally comprise one or more antioxidants, which may be present as constituents of the extender prior to contacting with the sperm, or which may be added to the sperm composition, each antioxidant in the concentration range of 0.01 mg/ml to 5 mg/ml.

A sperm cell sample can be extended to a predetermined concentration and/or towards a predetermined pH for use in the invention. Each of the predetermined concentrations and pH may be specific to different species, or even to different breeds of animals within a species to maintain cell viability. In one embodiment, the obtained sperm may be combined with a buffer in the form of a high capacity buffer. Exemplary buffers may include TRIS citrate, sodium citrate, sodium bicarbonate, HEPES, TRIS, TEST, MOPS, KMT, TALP, and combinations thereof. Any buffer having a high capacity for buffering pH may also be employed, and may be used in combination with additional components which promote sperm viability such as egg yolk, and sources of citrates or citric acid. The buffer may be set at a predetermined pH to normalize the pH of all the obtained sperm cell samples. In one embodiment, the buffer is adjusted to a pH of 7.2. Additionally, semen may become increasingly acidic over time, possibly due to proteins in the seminal fluid, or due to acidic by-products of dying or dead cells. The initial buffer introduces enough free proton (i.e., H+) binding sites to maintain pH near the predetermined target. Even in light of the natural tendency for sperm to become more acidic over time, the initial buffer provides a means for stabilizing pH prior to use in the invention. As one example, the obtained sperm sample may be diluted in the high capacity buffer in ratios from about 1:1 to about 1:10. The resulting sperm cell sample may have a sperm concentration many times below natural sperm concentrations for a particular species. The extended sperm may be centrifuged in order to re-concentrate the sperm cell sample prior to use with the invention. Centrifuging the sperm and removing supernatant allows the sperm to be re-concentrated into a predetermined concentration.

Manufacturing Improved Sperm Nuclei

One aspect of the invention comprises a staining media for manufacturing improved sperm nuclei. In one embodiment, the staining media comprises a buffer, a DNA selective dye and an aggregation-reducing compound. Any of the above-referenced buffers or other suitable buffer in the art, such as TRIS citrate, sodium citrate, sodium bicarbonate, HEPES, TRIS, TEST, MOPS, KMT, TALP, and combinations thereof, can be used.

Any DNA selective dye known in the art can be used, including but not limited to Hoechst 33342. In other embodiments, the staining media may be formed by using one or more UV or visible light excitable, DNA selective dyes as previously described in U.S. Pat. No. 5,135,759 and WO 02/41906, the contents of each of which are hereby incorporated by reference. Exemplary UV light excitable, selective dyes include Hoechst 33342 and Hoechst 33258.

Additionally, an aggregation-reducing compound may be added to prevent aggregation of sperm cells or sperm nuclei, as well as aggregation of midpieces and tails, to improve analysis via flow cytometry. Examples of aggregation-reducing compounds suitable for use in the invention include but are not limited to egg yolk, iodixanol, lecithin, bovine serum albumin, gelatin, collagen or hydrolyzed collagen, macromolecules such as arabinogalactan, and chemically defined polyethylene or polypropylene glycols. In a particular embodiment of the invention, the staining media can comprise 0.4% or more egg yolk. In another embodiment, the staining media can comprise between 1-30%, 1-20%, 1-15%, 1-10%, 1-5%, 1-3%, 1-2%, or 0.2-1%, egg yolk.

The staining media, or its separate components, can then be combined with a sperm cell sample to create a sperm cell mixture. Another aspect of the invention comprises sonicating the sperm cell mixture in order to remove midpieces and tails from the sperm heads to create sperm nuclei and to facilitate staining of the DNA within the sperm nuclei. In a particular embodiment of the invention, the sperm cell mixture is sonicated at a sufficient amplitude, frequency or duration to raise the temperature of the sperm cell mixture to more than 30, 40, 50, 60 or 70° C. in order to facilitate staining. In a particular embodiment, the temperature of the sperm cell mixture is raised to more than 50, 60 or 70° C. during sonication. In another embodiment, the temperature of the sperm cell mixture is raised to at least approximately 60° C. during sonication. In other embodiments, the target temperature during sonication can be 45° C. or 70° C., or can be in the range between 30-70° C. or 55-65° C. In another embodiment, sonication can be carried out on the sperm cell mixture for a particular duration to facilitate staining of sperm nuclei DNA. In one embodiment, the sperm cell mixture can be sonicated for a total of greater than 1, 2, 3, 4 or 5 minutes. In another embodiment, the sperm cell mixture can be sonicated for a total of 1-5 minutes or in an even more particular embodiment, approximately 2-3 minutes. In a further embodiment of the invention, once the sperm cell mixture is sonicated, the tails and midpieces are removed from the mixture via any known method in the art, including but not limited to filtration or centrifugation. The term "purifying" as used herein means removing debris, including cell debris such as sperm midpieces and tails, by for example centrifugation or filtration.

In a particular embodiment, the staining media is made by combining 98.0 ml of TRIS-based media, comprising 2% egg yolk, with 2.0 ml of Hoechst 33342 (8.1 mM of Hoechst 33342) to yield a final concentration of Hoechst 33342 of 160 μM in the staining media. 1.5 ml of this staining media is then combined with a sperm cell sample of 400 million sperm (extended or raw ejaculate) to create a sperm cell mixture. The sperm cell mixture is then sonicated for about 2 minutes or until it reaches a temperature of about 60° C. This sonication step acts to remove the midpieces and tails from the sperm cells to create sperm nuclei (i.e., sperm heads devoid of midpieces and tails) and to facilitate entry and binding of the DNA selective dye (in this case, Hoechst 33342) to the DNA within the sperm nuclei.

Because the sperm nuclei of the invention can be manufactured rapidly and locally, the need to use hazardous bacteriostatic preservatives such as sodium azide is eliminated. In one embodiment of the invention, the sperm cell mixture of the invention is free of any bacteriostatic preservative, including azide, sodium azide, or any derivatives thereof.

The phrase "unsorted sperm nuclei" as used herein means that neither the sperm nuclei, nor the sperm cells from which they are derived, have been subjected to a cell or particle sorting process.

Any suitable sonicator can be used to make the sperm nuclei of the invention. In a particular embodiment, a sonicator with a 20 mhz frequency can be used to make the sperm nuclei, such as Fisher Scientific Model FB120. In a more particular embodiment, the sonicator is set to an amplitude of 70%. Finally, one can check whether sonication was successful by examining the sonicated sperm cell mixture by microscope—the sonicated sperm cell mixture should substantially comprise sperm heads, with midpieces and tails removed and should be substantially free of intact sperm cells.

Using the Improved Sperm Nuclei in a Flow Cytometer

Based on the fluorescence emitted by a DNA selective dye upon exposure to a light source such as a high intensity laser beam, a flow cytometer (including a microfluidic device) is able to measure or quantify the amount of DNA present in each cell or nuclei stained with the DNA selective dye. Once the sperm cell mixture of the invention has been sonicated, it can be placed into a flow cytometer for analysis, including but not limited to, for the purpose of calibrating the flow cytometer. Accordingly, one aspect of the invention comprises a method using the improved sperm nuclei of the invention to calibrate a flow cytometer. In one embodiment, after sonication, a sperm cell mixture of the invention (now comprising sperm cell nuclei post-sonication), can be placed directly into a flow cytometer for analysis. Alternatively, after sonication, the sperm cell mixture can be further processed to separate the tails and midpieces from the stained sperm nuclei, by for example centrifugation, prior to being analyzed in a flow cytometer. One embodiment of the invention comprises using the signal generated by the analysis of the improved sperm nuclei to calibrate the flow cytometer. "Calibrating" or "calibration" in the context of the invention means adjusting a flow cytometer parameter to increase the accuracy or precision of the flow cytometer. The invention encompasses calibrating flow cytometers used for cell or particle analysis (e.g., determining sex-chromosome purity in a sorted sperm cell sample, or detection of the presence or absence of a chromosomal aberration), as well as flow cytometers used for cell or particle sorting (e.g. sex sorting a sperm cells sample, or ablating or photo-damaging sperm cells bearing the undesired sex chromosome).

Commonly used and well known sperm analysis and sorting methods via flow cytometry are exemplified by and described in U.S. Pat. Nos. 5,135,759, 5,985,216, 6,071,689, 6,149,867 and 6,263,745; International Patent Publications WO 99/33956 and WO 01/37655; and U.S. patent application Ser. No. 10/812,351 (corresponding International Patent Publication WO 2004/088283), the content of each of which is hereby incorporated herein by reference.

One of the difficulties in accurate quantification of sperm DNA using fluorescence—as required to effectively differentiate sperm cells on the basis of which sex chromosome they are carrying—is the geometry of the sperm head, which is shaped like a paddle in most species. Generally, the intensity of the laser beam and the intensity of fluorescence is lowest when the flat face of the sperm is oriented away from a fluorescence detector. This flat orientation actually results in the most accurate measure of DNA content within a cell. Thus, if one desires to measure the DNA content of as many cells in a population of cells as possible and as accurately as possible—for example to effectively sex sort sperm cells—it is necessary that as many cells as possible are properly oriented (i.e., the flat face of the sperm cells facing the laser beam and the detector) when fluorescence detection occurs. There are many techniques known in the art used to orient sperm using various forces generated by the flow cytometer and/or microfluidic device, all of which are contemplated for use with the invention. One way in which orientation can be accomplished in a flow cytometer is by using an orienting nozzle such as described in U.S. Pat. No. 6,357,307, which is hereby incorporated by reference in its entirety. In the context of sex sorting applications, two detectors are generally used for detecting fluorescence emitted by sperm cells. The detectors translate the collected emissions into electrical signals, which are analyzed using analog or digital systems to classify the particles according to selected characteristics of the particles, such as the angle of the sperm head as it traverses the laser beam and the X/Y chromosome content of sperm cells. One of the detectors is oriented at 0° relative to the optical axis of the laser beam or other source of electromagnetic radiation and is used to measure forward fluorescence, which corresponds to cell DNA content. The second detector is oriented 90° relative to the optical axis of the laser beam or other source of electromagnetic radiation and is used to measure side fluorescence, which corresponds to the orientation of the sperm. Since the fluorescence signal is highest for sperm oriented with their paddle edge toward the side fluorescence detector, only the sperm that emit peak fluorescence to the side fluorescence detector are considered properly oriented, generally. These properly oriented cells will provide the most accurate picture of their DNA content when detected by the forward fluorescence detector. It is equally important that the laser beam and the forward fluorescence detector are fully facing the flat side of the sperm. Conversely, cells that are not properly oriented will provide a less accurate picture of their DNA content, making a determination of which sex chromosome they are carrying more difficult if not impossible. Thus, when trying to produce a subpopulation of sperm cells that bear a particular sex chromosome, it is often desirable to select only those sperm cells that are properly oriented for the sorting phase or conversely to exclude sperm cells that failed to orient properly from the sorting phase. This can be accomplished by creating a gate.

Flow cytometry or microfluidics based cell sorting and data analysis are based on the principle of gating. Typically, gates are created around populations of cells with common characteristics. In the context of the invention, these characteristics include forward fluorescence and side fluorescence. Once a gate is created, the cells encompassed by the gate, or excluded by the gate, can be subjected to further analysis or processing. Generally, the first step in gating when sorting sperm is distinguishing populations of sperm based on their forward and side fluorescence properties. As noted above, forward and side fluorescence provide an estimate of the DNA content of the cells and their orientation, respectively. Unoriented sperm will generate events having a lower level of side fluorescence and forward fluorescence, as noted above. If a quenching dye is used, non-viable sperm will generate events having a lower level of both forward and side fluorescence due to the presence of the quenching dye within these cells.

In one embodiment of the invention, the events generated by a population of sperm cells are depicted on a bivariate plot, with forward fluorescence and side fluorescence measured along the Y and X axes, respectively. Accordingly, unoriented sperm cells can be differentiated from oriented sperm cells by their relative positions on such a bivariate plot. By placing a gate around the events generated by an oriented subpopulation, one is able to subsequently remove or separate those gated sperm cells from the unoriented sperm cells. Alternatively, placing a gate around the unoriented sperm cells would also allow one to remove or separate those sperm cells from the oriented sperm cells. Generally, gates can be applied either to exclude subpopulations from further analysis, processing or examination or to select subpopulations for further analysis, processing or examination. Using analytical software, measurements and statistics can be obtained for various parameters in addition to the number of cells and percentage of cells within a gate. This can include such measurements as median and mean fluorescence intensity. Two-parameter density plots display two measurement parameters, one on the x-axis and one on the y-axis and the events as a density (or dot) plot.

A gated subpopulation of oriented sperm cells can, for example, be subsequently sex sorted, i.e., further processed to separate X chromosome bearing sperm from Y chromosome bearing sperm. This is generally accomplished by placing a subsequent gate around either the X chromosome bearing sperm cell subpopulation or the Y chromosome bearing sperm cell subpopulation, which are distinguishable via fluorescence intensity when using a DNA selective dye due to the presence of a larger of quantity of DNA in X chromosome bearing sperm cells. Techniques for flow cytometrically sex-sorting sperm are well known in the art, as exemplified by and described in U.S. Pat. No. 9,347,038, whose disclosure with respect to sex sorting sperm cells via flow cytometry is incorporated by reference herein. In a particular embodiment of the invention, a first gate is placed around a subpopulation of oriented sperm cells, and then within that subpopulation of oriented sperm cells, a subsequent gate is placed around either an X chromosome bearing subpopulation or a Y chromosome bearing subpopulation, and one or both of the X chromosome bearing subpopulation and the Y chromosome bearing subpopulation are collected in separate collection containers. The sex purity of the collected sex chromosome bearing subpopulation is typically 51-75%, 55-75%, 51-80%, 51-85%, greater than 90%, greater than 92%, or greater than 95%.

It is typically the case that during the manufacture of sex sorted sperm, the sex purity of the product is tested at various phases of the process to ensure that it meets the purity at which it will be marketed. Sex purity is often tested in the post-sort stream containing sperm cells with the desired sex chromosome, in the catch fluid containing sperm cells with the desired sex chromosome or in a semen straw containing sperm cell with the desired sex chromosome. Sex purity is typically assessed on a different flow cytometer than the one that performed the sorting, although it can be assessed on the same flow cytometer that performed the sorting. For high resolution analysis such as sex purity, higher laser power is required, while the commercial sorter uses lower power laser energy to maintain sperm health. Accordingly, in commercial sorting, the flow cytometer that is tasked with assessing sex purities is generally dedicated to that task and does not have the additional components needed to sort cells.

In certain embodiments of the invention, sorting of sperm may be accomplished using any process or device known in the art for cell sorting including but not limited to use of a flow cytometer or use of a microfluidic chip, and optionally encompasses techniques for physically separating sperm from each other, as with droplet sorting and fluid switching sorting, and techniques in which sperm bearing the undesired sex chromosome are killed, immobilized, or otherwise rendered infertile, such as by use of laser ablation/photo-damage techniques.

A sperm sample to be analyzed via a flow cytometer or microfluidic device is contained in a sample fluid. A sheath fluid is generally used in a flow cytometer or microfluidic device to hydrodynamically focus, entrain or orient sperm cells in the sample fluid. Generally, the sheath fluid is introduced into a nozzle of a flow cytometer or into a microfluidic device using pressurized gas or by a syringe pump. The pressurized gas is often high quality compressed air. In certain embodiments of the invention, a stream containing sperm to be analyzed may be comprised of a sample fluid and a sheath fluid, or a sample fluid alone. Optionally, the sample fluid or sheath fluid may also contain an additive, such as, one or more antioxidants, an antibiotic or a growth factor, as discussed above with respect to sperm sample collection. Each of these additives may be added to either fluid in accordance therewith.

FIG. 1 illustrates, in schematic form, part of a flow cytometer used to analyze and then sort a sperm composition to form one or more subpopulations, the flow cytometer being generally referenced as 10. The flow cytometer 10 of FIG. 1 can be programmed by an operator to generate two charged droplet streams, one containing cells within a center sort region charged positively 12, for example, one containing cells within a flanking sort region charged negatively 13 for example, while an uncharged undeflected stream of indeterminate cells 14 simply goes to waste, each stream collected in receptacles 28, 29, and 30, respectively.

Initially, a stream of sperm under pressure, is deposited into the nozzle 15 from the sperm source 11 in a manner such that they are able to be coaxially surrounded by a sheath fluid supplied to the nozzle 15 under pressure from a sheath fluid source 16. An oscillator 17 which may be present can be very precisely controlled via an oscillator control mechanism 18, creating pressure waves within the nozzle 15 which are transmitted to the coaxially surrounded sperm stream as it leaves the nozzle orifice 19. As a result, the exiting coaxially surrounded sperm stream 20 could eventually and regularly form droplets 21.

The charging of the respective droplet streams is made possible by the cell sensing system 22 which includes a laser 23 which illuminates the nozzle exiting stream 20, and the light emission of the fluorescing stream is detected by a sensor 24. The information received by the sensor 24 is fed to a sorter discrimination system 25 which very rapidly makes the decision as to whether to charge a forming droplet and, if so, which charge to provide the forming drop and then charges the droplet 21 accordingly. The charged or uncharged droplet streams pass between a pair of electrostatically charged plates 26, which cause them to be deflected either one way or the other, or not at all, depending on their charge into respective collection vessels 28 and 29 to form a subpopulation of sperm cells that fell within the center sort region and a subpopulation of cells that fell within the flanking sort region, respectively. The uncharged non-deflected sub-population stream containing indeterminate or undesired cells go to the waste container 30.

Figure 2:
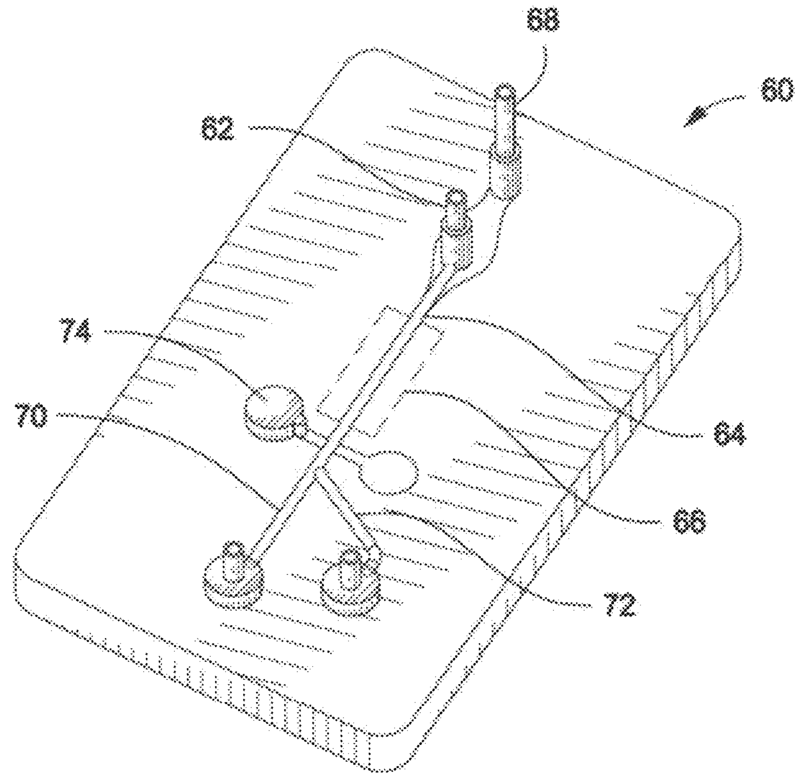
FIG. 2 is a schematic depiction of a microfluidic device.

Turning now to FIG. 2, an alternative particle sorting instrument is partially illustrated in the form of a microfluidic chip 60. The microfluidic chip 60 may include a sample inlet 62 for introducing sample containing particles or cells into a fluid chamber 64 and through an inspection zone 66. Sample introduced through the sample inlet 62 may be insulated from interior channel walls and/or hydrodynamically focused with a sheath fluid introduced through a sheath inlet 68. Sample may be interrogated at the inspection zone 66 with an electromagnetic radiation source (not shown), such as a laser, arc lamp, or other source of electromagnetic electricity. Resulting emitted or reflected light may be detected by a sensor (not shown) and analyzed with an analyzer (not shown). Each of the sheath pressure, sample pressure, sheath flow rate, and sample flow rate in the microfluidic chip may be manipulated in a manner similar to a jet-in-air flow cytometer, by either automatic adjustments performed by the execution of written instructions in the analyzer or by manual adjustments performed by an operator.

In certain embodiments of the invention, once inspected, particles or cells in the fluid chamber 64 may be mechanically diverted from a first flow path 70 to a second flow path 72 with a separator 74, for altering fluid pressure or diverting fluid flow. The particles or cells may also be permitted to continue flowing along the first flow path 70 for collection. The illustrated separator 74 comprises a membrane which, when depressed, may divert particles into the second flow path 72. Other mechanical or electro-mechanical switching devices such as transducers and switches may also be used to divert particle flow.

In flow cytometers for use in the invention, beam shaping optics may be used to manipulate the shape of a beam spot produced by a laser beam or other source of electromagnetic energy by, for example, manipulating the aspect ratio, or the vertical and horizontal aspects of the beam spot to address the issues of greatly varied laser power exposure experienced by the sperm and coincident excitation of fluorochrome bound to multiple DNAs. International Publication No. WO 01/85913 and U.S. Pat. No. 7,371,517, which are incorporated by reference herein in their entirety, describe embodiments that employ beam shaping optics to increase the area and reduce the height of a conventional irradiation beam pattern.

Instead of having charged plates 26 for physically separating sperm cell subpopulations from each other, a flow cytometer for sex sorting for use with the invention may include an ablation laser for damaging or photo-ablating sperm cell having the undesired sex chromosome. Specifically, the ablation laser may be timed to kill, damage, or deactivate sperm in a fluid stream based upon a certain classification or characteristic, which in the context of sex sorting is the presence or absence of a particular sex chromosome. For example, if it is desired to generate a population of sperm having a skewed ratio of viable X chromosome bearing sperm, then the ablation laser may be used to damage or kill Y chromosome bearing sperm in the fluid stream. On the other hand, if it is desired to generate a population of sperm having a skewed ratio of viable Y chromosome bearing sperm, then the ablation laser may be used to damage or kill X chromosome bearing sperm in the fluid stream. In this way, laser ablation may be used as a technique to isolate, separate, select, classify or sort particles, cells, sperm cells or the like based upon particle or cell characteristics.

One aspect of the improved sperm nuclei of the invention is their use in calibrating a flow cytometer. Calibrating a flow cytometer for use in the invention encompasses aligning the excitation and emission paths in the flow cytometer, which in a jet-in-air flow cytometer typically involves establishing a stream location and beam shape that maximizes the intensity of events in terms of either forward fluorescence or side fluorescence, or both.

In a jet-in-air flow cytometer used for sex sorting or sex purity analysis, the side fluorescence detector, and its associated side fluorescence collection objective and pinhole aperture, typically have a fixed location in the device. Generally, the stream (i.e., jet), exiting the nozzle is first aligned with the pinhole aperture by illuminating the stream, thereby projecting its profile onto the pinhole aperture. If the stream profile is not aligned with the pinhole aperture, the stream location can be adjusted by adjusting the position of the nozzle via a stream positioning stage to which the nozzle is mounted. The stream positioning stage generally has three axes of movement—two axes of movement in a horizontal plane and a third axis of movement along a vertical plane that is perpendicular to the horizontal plane. The angle of the nozzle's orifice (i.e., the angle of the longitudinal axis of the exiting stream) can also be independently adjusted via two gimbals on the stream positioning stage. Stream verticality can be confirmed by adjusting the nozzle location upwards in the vertical plane. If the stream image moves out of focus or migrates left or right in relation to the pinhole aperture, the stream is not in alignment with the pinhole aperture (or with the side fluorescence detector or the side fluorescence collection objective). Once stream verticality is confirmed, the nozzle tip location can be adjusted, which is typically adjusted until it is just in view of the projected image.

Once the stream is coarsely aligned with the side fluorescence detector as set forth above, the beam shaping optics can be adjusted to maximize the intensity of events in terms of either forward fluorescence or side fluorescence, or both. The beam shaping optic stage to which the beam shaping optics are mounted generally has three axes of movement—two axes of movement in a horizontal plane and a third axis of movement along a vertical plane perpendicular to the horizontal plane.

Once the beam shaping optics are coarsely aligned, the locations of the forward fluorescence detector or the forward fluorescence collection objective can be adjusted to maximize the intensity of events in terms of either forward fluorescence or side fluorescence, or both. The forward fluorescence detector generally has one axis of movement along a vertical plane. The forward fluorescence collection objective generally has three axes of movement—two axes of movement in a horizontal plane and a third axis of movement along a vertical plane that is perpendicular to the horizontal plane.

Once a flow cytometer has been coarsely aligned, any of the above flow cytometer parameters, including but not limited to, stream or jet location and angle, beam shape and the locations of the forward fluorescence detector or the forward fluorescence collection objective, can be adjusted to achieve fine alignment to maximize the intensity of events in terms of either forward fluorescence or side fluorescence, or typically both. Additionally, the gain or voltages for the forward fluorescence and side fluorescence detectors can be adjusted to maximize intensity.

Figure 3:
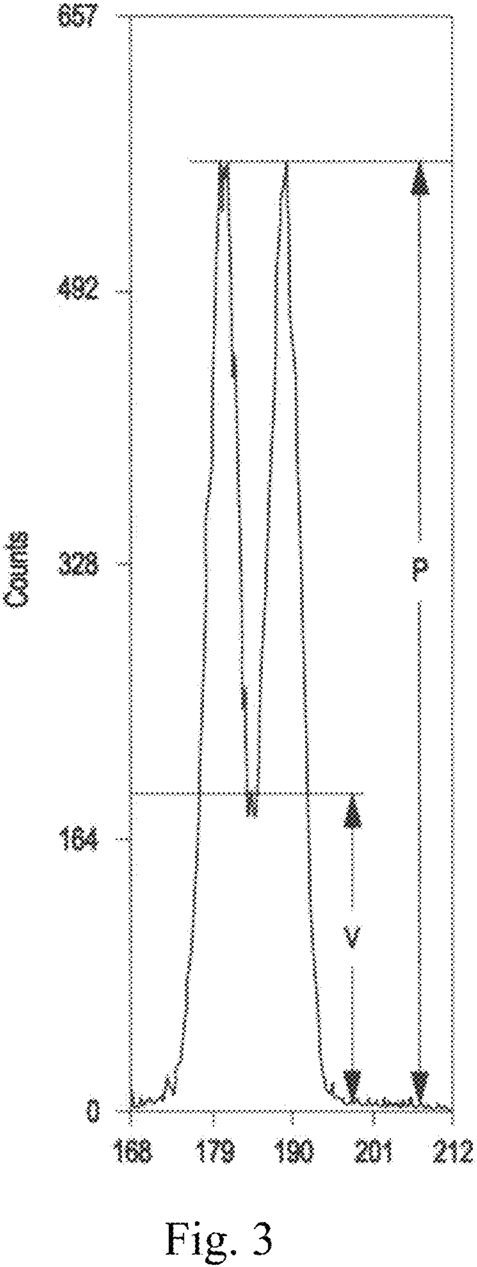
FIG. 3 is a depiction of a histogram of forward fluorescence intensities.

The invention contemplates that calibration can be carried out either manually or automatically. In addition to maximizing the intensity of events, as can be seen on a two-parameter density plot of forward florescence intensity and side fluorescence intensity, alignment can be adjusted to increase the peak to valley ratio (PVR), or to decrease the coefficient of variation (CV), present in a population of sperm nuclei of the invention as can be seen on a univariate plot of their forward fluorescence intensities. Generally, two-parameter density plots (i.e., bivariate plots) display two measurement parameters, one on the x-axis and one on the y-axis and the events as a density (or dot) plot. The parameters can include forward florescence intensity, side fluorescence intensity and an integral of forward florescence intensity. In some embodiments, a flow cytometer is considered calibrated based on achieving a threshold value for PVR, CV, or percentage of oriented cells, when analyzing the improved sperm nuclei of the invention. In a particular embodiment, a flow cytometer is considered calibrated when the sperm nuclei of the invention generate a histogram of forward fluorescence having a PVR of at least 80%, 85% or 90% when at least 80%, 85% or 90% of events generated by the sperm nuclei are gated. FIG. 3 illustrates a univariate plot in the form of a histogram that may be produced by the analyzer 36 and generated into a graphical presentation for an operator based on the signal generated by analysis of the sperm nuclei. The data illustrated in FIG. 3 may represent the number of occurrences of peak signal intensities from the side or forward fluorescence within a certain period. In the case of sperm, X chromosome bearing sperm and Y chromosome bearing sperm tend to have peak intensities that vary by between 2 and 5%, depending on the species, and this difference is reflected in the bimodal distribution of peak intensities. Because X chromosome bearing sperm and Y chromosome bearing sperm tend to have differing fluorescence values, each of the peaks represents either X chromosome bearing sperm of Y chromosome bearing sperm. FIG. 3 further illustrates the concept of the PVR, which is derived from a relative intensity measurement at the lowest point between the two groups, the valley, which may be considered a value V, and a second relative intensity measurement at the peak or peaks of the histogram at P.

Example 1

This example provides one embodiment of a method of manufacturing the sperm nuclei of the invention. 98.68 ml of TRIS-based media was combined with 1.34 ml of Hoechst 33342 dye (8.1 mM) to form a first composition. 98 ml of this first composition was then combined with 2 ml of egg yolk to form the final staining media. A raw ejaculate was obtained from a bovine bull on which a NucleoCount (ChemoMetec) was performed to obtain sperm cell concentration. 1.5 ml of the final staining media was placed into a 5 ml conical tube, combined with 400 million sperm cells and then vortexed to form a sperm cell mixture. This sperm cell mixture was then sonicated for 2 minutes until the tube was hot to the touch (approximately 60° C.) using a sonicator with a 20 mhz frequency (Fisher Scientific Model FB120) and set to an amplitude of 70%.

Example 2

Figure 4:
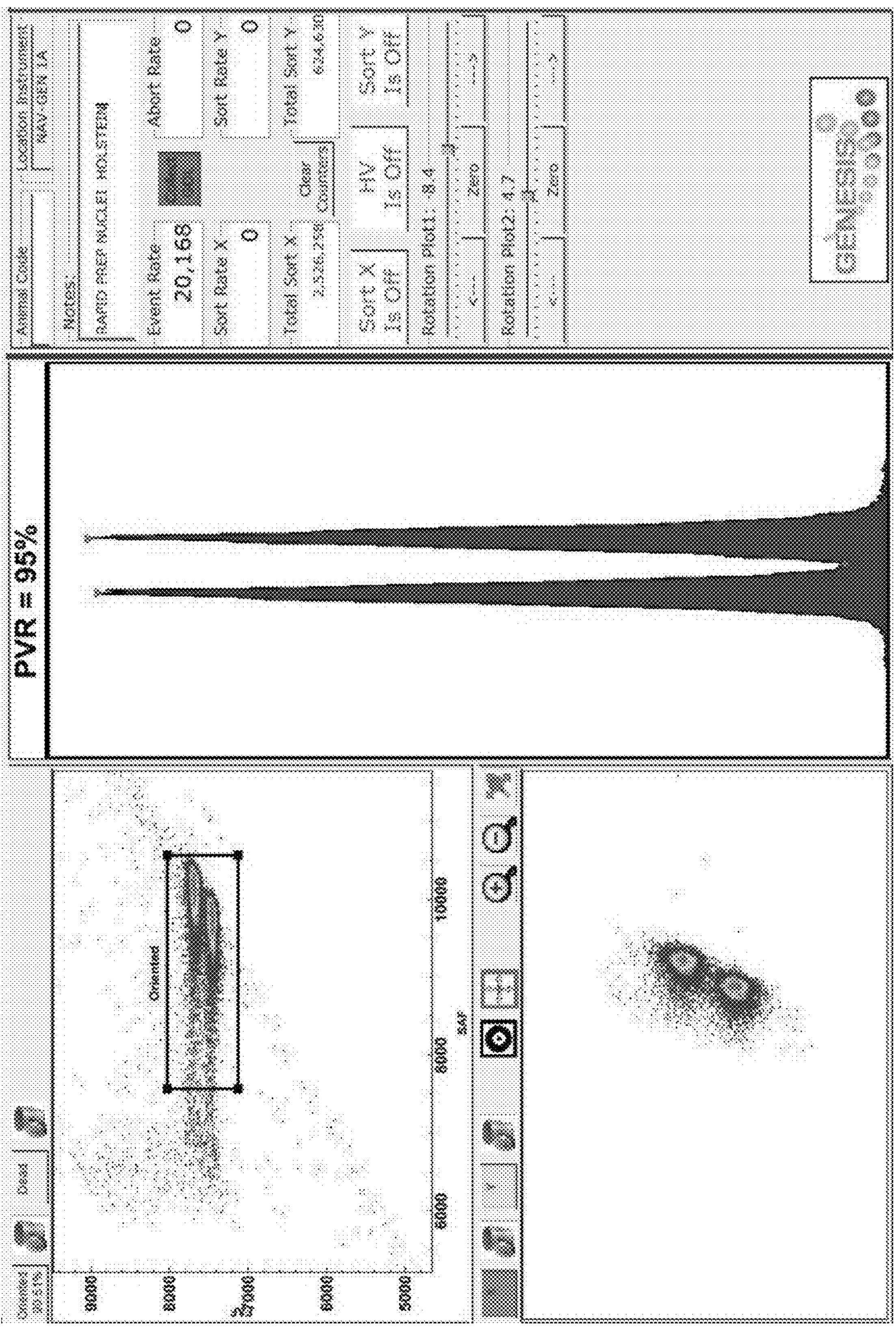
FIG. 4 is a screenshot from a flow cytometer aligned using sperm nuclei of the invention derived from a first Holstein bull.
Figure 5:
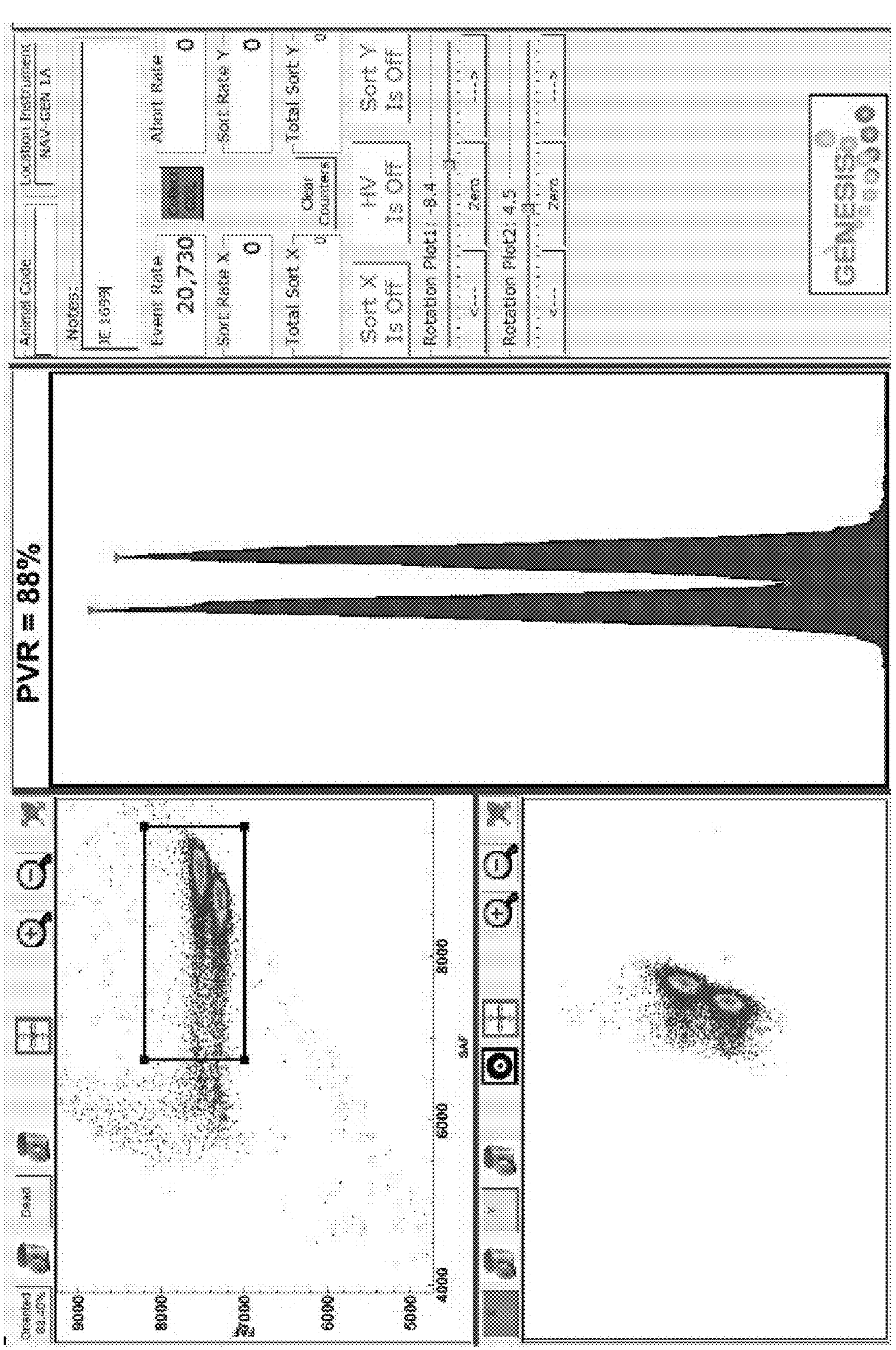
FIG. 5 is a screenshot from a flow cytometer aligned using sperm nuclei of the invention derived from a Jersey bull.
Figure 6:
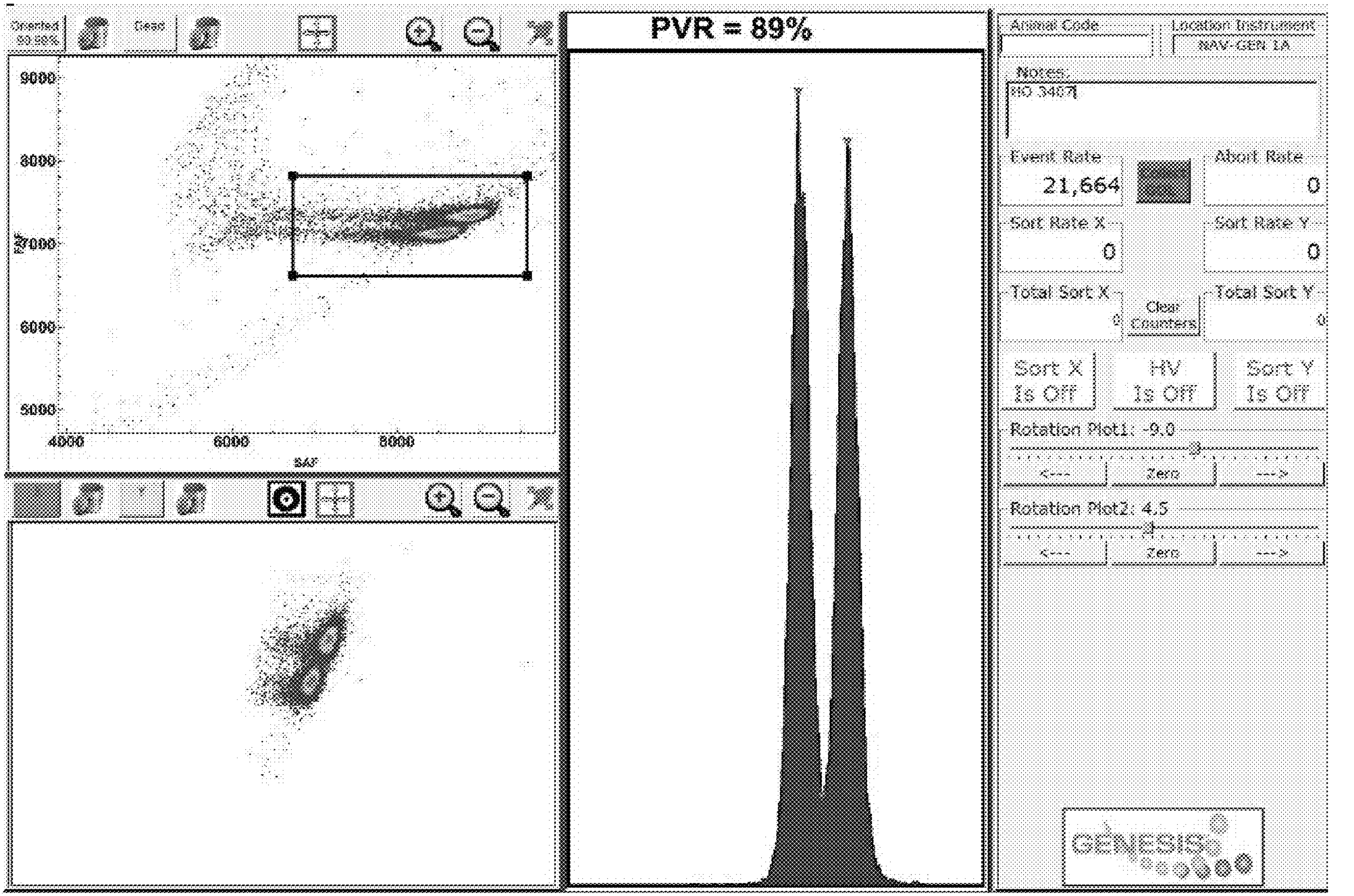
FIG. 6 is a screenshot from a flow cytometer aligned using sperm nuclei of the invention derived from a second Holstein bull.
Figure 7:
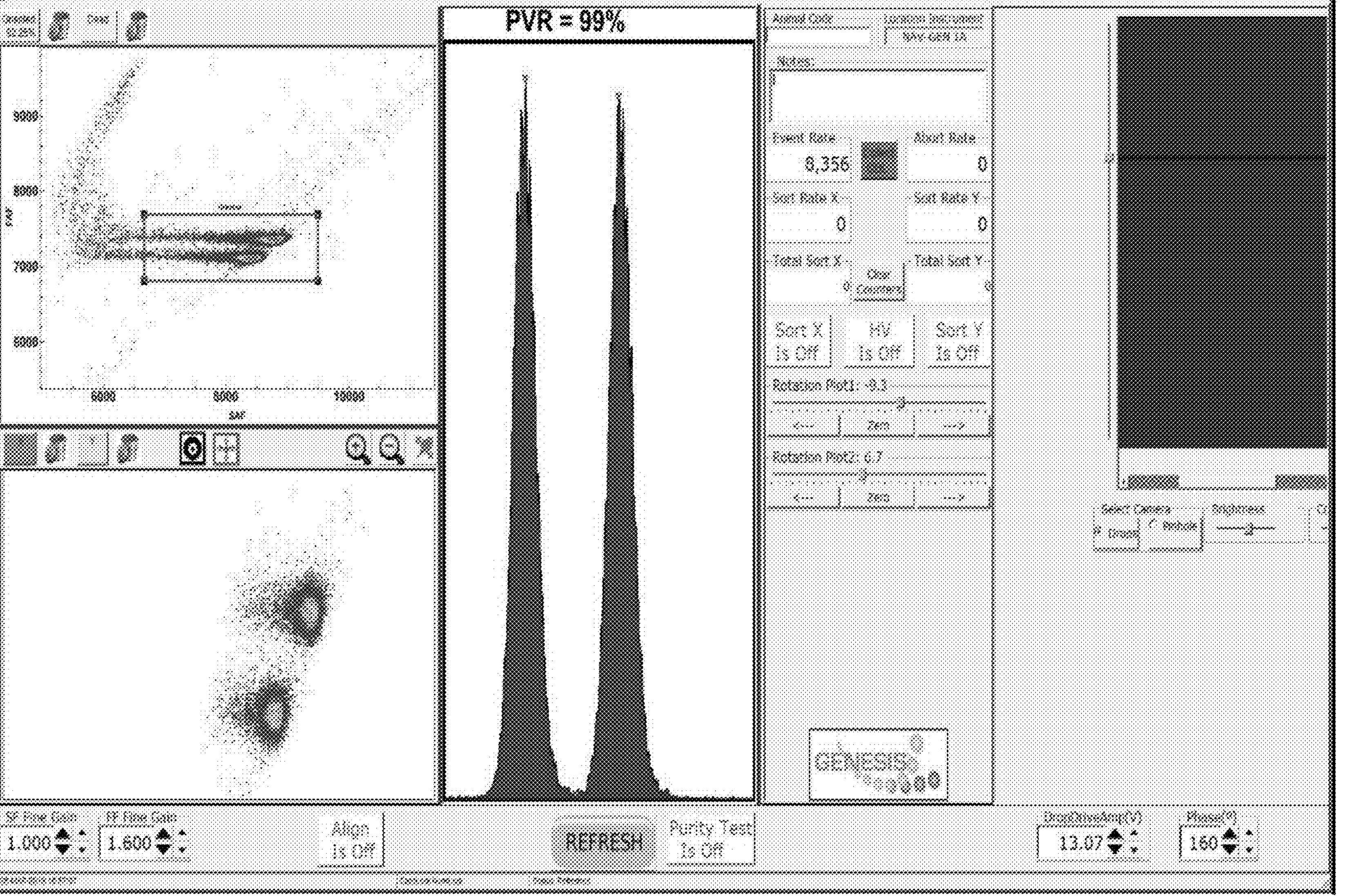
FIG. 7 is a screenshot from a flow cytometer aligned using sperm nuclei of the invention derived from a goat.

In Example 2, sperm nuclei of the invention were prepared in accordance with Example 1 and then used to align a jet-in-air flow cytometer used for sex purity analysis (Genesis I, Cytonome/ST, LLC) at an event rate of about 20,000 events per second. Four sperm nuclei samples were each derived from ejaculates from two Holstein bulls, one Jersey bull and one goat, respectively. After alignment, screen shots from the flow cytometer (see FIGS. 4-7) were obtained for each sperm nuclei sample (FIGS. 4 and 6 corresponding to each Holstein bull sample; FIG. 5 corresponding to the Jersey bull sample; and FIG. 7 corresponding to the goat sample). Each of these Figures shows two bivariate plots (forward fluorescence intensity ("FAF") vs side fluorescence intensity ("SAF") displayed in the upper left corner of the screen shot and forward fluorescence vs integrated forward fluorescence displayed in the lower left corner of each screenshot; and a univariate plot showing a histogram of forward fluorescence intensities in the middle of the screen shot. Flow cytometer parameters adjusted during alignment included stream location, beam shape and the locations of the forward fluorescence detector or the forward fluorescence collection objective. For each sample, beam and stream alignment were adjusted to obtain maximum forward and side fluorescent intensities and maximum PVR.

Conventional sperm nuclei were also prepared for comparison to the sperm nuclei of the invention as follows. Ejaculates from 45-50 Holstein bulls were collected and frozen on the day of collection in 15 ml Conical Falcon tubes. Samples were thawed and total semen volume was measured. Semen was then pooled as follows. Using a 1 ml pipette, semen from each 15 mL tube was gently remove and pooled into a pre-weighed 500 ml glass beaker. Using very small quantities of TRIS AZIDE to rinse out the residual sperm in tubes, all sperm was transferred into the beaker and then stirred gently with a magnetic stir plate. The mixture comprised about 50% ejaculate and 50% TRIS AZIDE and had about 600-800 million sperm per ml (determined by Nucleocounter (ChemoMetec). The sperm mixture was distributed into 50 ml Falcon Tubes, each containing 40-45 ml, and then centrifuged for 10 minutes at 850 G (Eppendorf 5810R) in a cold room. The supernatant (seminal fluid) was then decanted. Using limited amounts of TRIS AZIDE, the pellets were resuspended to concentrations of about 4 billion sperm per ml and about 25-30 ml of the resuspended sperm were placed into individual Falcon Tubes. Each tube was sonicated for a total of 15 minutes. The 50 ml tubes of sonicated sperm were then filled to 45 ml with cold TRIS AZIDE, and centrifuged for 15 minutes at 850 G. The supernatant with tail fragments was decanted and the pellet resuspended in 20 ml of cold TRIS AZIDE media by using about 1.0-1.5 minutes of sonication. Tubes were then topped off to 45 ml with TRIS AZIDE media and centrifuged for 6-10 minutes at 850 G. This step was repeated about 6-8 times. As the samples became cleaner, the pellets were pooled into a smaller number of tubes, for example, 4 then 2 then 1. At the end of this process, nuclei were diluted and viewed under the microscope to look for midpieces and tail fragments. The nuclei were resuspended into TRIS AZIDE in 50 ml Falcon tubes at a concentration of 6-7 billion nuclei per ml. The final product was suspended in TRIS AZIDE at a concentration of 200 million nuclei per ml. This concentration was reached by careful additions of TRIS AZIDE in small steps. The nuclei in TRIS AZIDE (pH 6.8) at 200 million per ml were then stained with about 6 μl of Hoechst 33342 (8.1 mM or 5 mg/ml) for each ml of sperm nuclei and incubated for 60+ minutes at 34° C. Aliquots of 3 ml of stained sperm nuclei were then placed into sample tubes.

Figure 8:
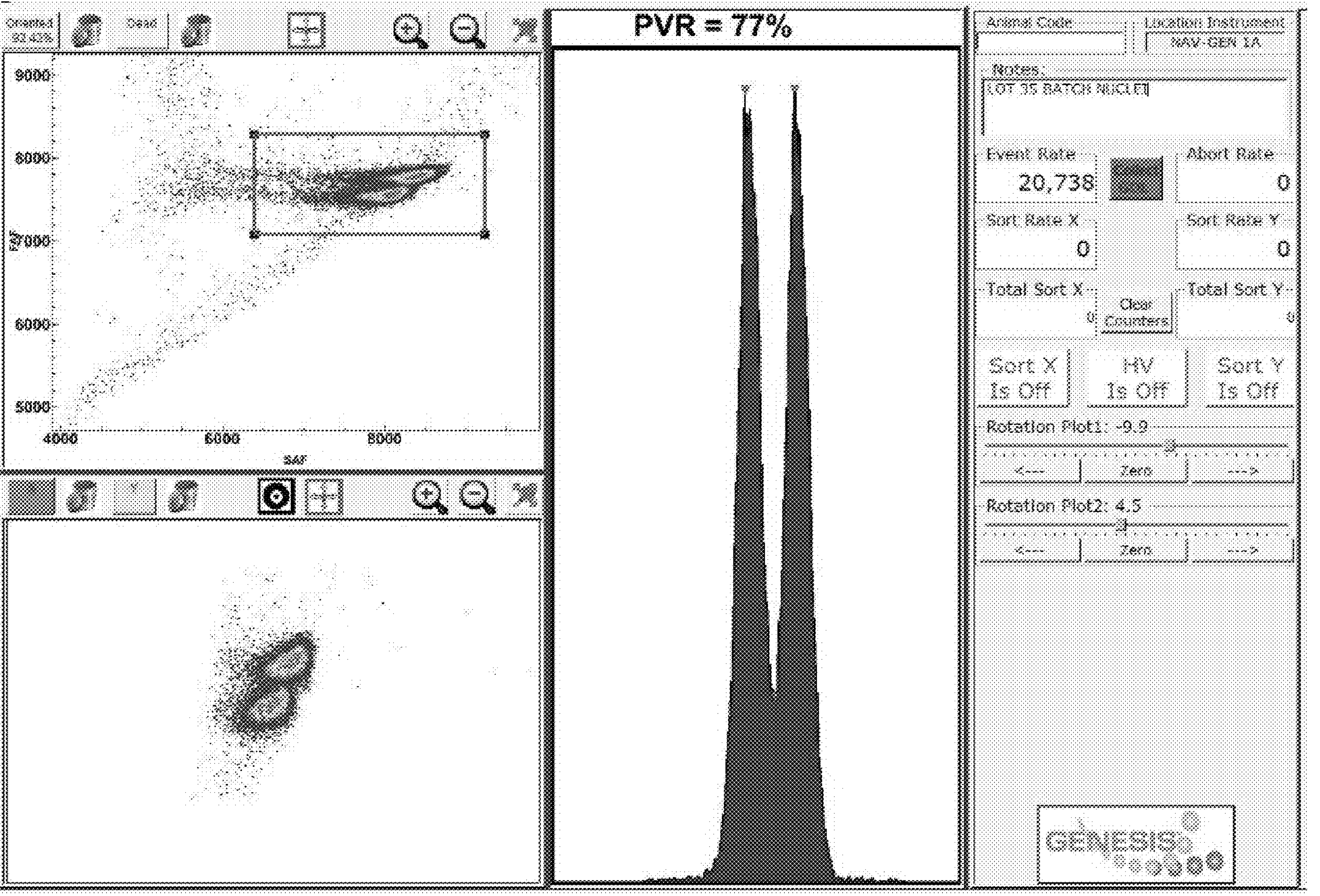
FIG. 8 is a screenshot from a flow cytometer aligned using conventionally prepared sperm nuclei derived from a mix of many Holstein bulls.

A sample tube of these conventionally prepared sperm nuclei was then used to align a jet-in-air flow cytometer used for sex purity analysis (Genesis I, Cytonome/ST, LLC) at an event rate of about 20,000 events per second. The results after alignment can be seen in FIG. 8, which shows a screenshot from the flow cytometer. The conventionally prepared sperm nuclei were only able to generate a PVR of 77%, compared to PVRs of 88-99% (see FIGS. 4-7) obtained using the sperm nuclei of the invention.

What we claim is:

1. A method of processing sperm cells comprising providing an unsorted sperm cell sample;

combining a DNA selective dye and an aggregation-reducing compound with the unsorted sperm cell sample to create a sperm cell mixture; and sonicating the sperm cell mixture to create stained sperm nuclei, wherein the sperm cell mixture has a temperature of 45° C. or greater during the step of sonication.

2. The method of claim 1, wherein the DNA selective dye is Hoechst 33342.

3. The method of claim 1, wherein the unsorted sperm cell sample is obtained from one male.

4. The method of claim 1, wherein the aggregation-reducing compound is egg yolk.

5. The method of claim 1, wherein the method is completed in 20 minutes or less.

* * * * *